United States Patent
Heuer (10) Patent No.: US 10,702,316 B2
(45) Date of Patent: Jul. 7, 2020

(54) HANDLING INSTRUMENT FOR A BONE SCREW

(71) Applicant: SILONY MEDICAL INTERNATIONAL AG, Frauenfeld (CH)

(72) Inventor: Frank Heuer, Filderstadt (DE)

(73) Assignee: SILONY MEDICAL INTERNATIONAL AG, Frauenfeld (CH)

(*) Notice: Subject to any disclaimer, the term of this patent is extended or adjusted under 35 U.S.C. 154(b) by 172 days.

(21) Appl. No.: 15/771,678

(22) PCT Filed: Nov. 10, 2016

(86) PCT No.: PCT/EP2016/077289
§ 371 (c)(1),
(2) Date: Apr. 27, 2018

(87) PCT Pub. No.: WO2017/089141
PCT Pub. Date: Jun. 1, 2017

(65) Prior Publication Data
US 2018/0325565 A1      Nov. 15, 2018

(30) Foreign Application Priority Data
Nov. 26, 2015   (DE) ................. 10 2015 223 479

(51) Int. Cl.
*A61B 17/70* (2006.01)
*A61B 17/88* (2006.01)
(52) U.S. Cl.
CPC ...... *A61B 17/7082* (2013.01); *A61B 17/7037* (2013.01); *A61B 17/8875* (2013.01)
(58) Field of Classification Search
CPC .................................................. A61B 17/7082
See application file for complete search history.

(56) References Cited

U.S. PATENT DOCUMENTS

| 8,795,283 B2 | 8/2014 | Petit |
| 9,289,249 B2* | 3/2016 | Ramsay ............ A61B 17/7092 |

(Continued)

FOREIGN PATENT DOCUMENTS

EP      2692304 A1      2/2014

OTHER PUBLICATIONS

International Search Report and Written Opinion Form PCT/ISA210 and PCT/ISA/237, International Application No. PCT/EP2016/077289, pp. 1-12, International Filing Date Nov. 10, 2016, dated Feb. 8, 2017.

*Primary Examiner* — Andrew Yang
(74) *Attorney, Agent, or Firm* — Bond Schoeneck & King, PLLC; George McGuire (57) ABSTRACT

The invention relates to a handling instrument for a pedicle screw. The handling instrument is connectable to the pedicle screw in a rigid and rotationally fixed manner. The handling instrument includes a housing part which extends in an axial longitudinal direction and which is tubular or sleeve-shaped in some sections, and a rod part, which is arranged in the outer housing part and which can engage into a tool placement point of the pedicle screw. The housing part has a guide slot, and the rod part has a transverse opening, which extends in a radial direction, in particular in the region of the guide slot of the housing part. A coupling element can be arranged in the transverse opening of the rod part arranged in the housing part, and the coupling element protrudes into the guide slot of the housing part and can be moved in the guide slot in the longitudinal direction in a sliding manner such that the rod part and the housing part can be moved relative to each other in the longitudinal direction while being rotationally fixed to each other by means of the coupling element.

25 Claims, 9 Drawing Sheets

(56) References Cited

U.S. PATENT DOCUMENTS

| | | |
|---|---|---|
| 2004/0138662 A1 | 7/2004 | Landry et al. |
| 2006/0200132 A1 | 9/2006 | Chao et al. |
| 2009/0163963 A1 | 6/2009 | Berrevoets |
| 2009/0234395 A1 | 9/2009 | Hoffman et al. |
| 2013/0110179 A1 | 5/2013 | Barrus et al. |

* cited by examiner

HANDLING INSTRUMENT FOR A BONE SCREW

CROSS-REFERENCE TO RELATED APPLICATIONS

This application is the United States National Phase Application of PCT Application Number PCT/EP2016/077289, filed Nov. 10, 2016 which in turn claims priority to German Application No. DE102015223479.7, filed Nov. 26, 2015 the entire disclosure of which is incorporated herein by reference.

The present invention relates to a handling instrument for a bone screw, in particular a pedicle screw, the bone screw comprising a threaded shaft and a head, in particular a fork head, and it being possible to connect the handling instrument to the bone screw in a releasable yet rigid and rotationally fixed manner, such that the threaded shaft of the bone screw can be screwed into a bone by means of the handling instrument, said handling instrument comprising an outer housing part that extends in the longitudinal direction, is designed at least in portions in the shape of a tube or sleeve and comprises a wall, and said handling instrument comprising an inner, in particular cannulated, rod part that is arranged in the outer housing part, the inner rod part being able to engage in a torque-absorbing tool placement point of the bone screw.

When mention is made in the following of a longitudinal direction, the axial longitudinal direction is meant. The circumferential direction is concentric with respect to the axial longitudinal direction, and the radial direction is perpendicular to the axial longitudinal direction. The handling instrument comprises a distal and a proximal end, which is opposite said distal end in the longitudinal direction, the handling instrument being connectable to the bone screw in the region of the distal end. "Distally" means towards the distal end of the handling instrument and "proximally" means towards the proximal end of the handling instrument.

Instruments of this kind for screwing in bone screws into a bone are known from the prior art, for example from U.S. Pat. No. 8,100,916 B2. A disadvantage of known handling instruments is that the torque for screwing in the bone screw is introduced only via the central rod part and a tool placement point of the bone screw. Furthermore, the known instruments engage in an internal thread on the head of the bone screw so as to hold the head of the bone screw in a stable manner relative to the threaded shaft during screwing-in. This can damage the internal thread.

The object of the present invention is to design a handling instrument such that the kinematics when connecting the handling instrument to the bone screw and when screwing the bone screw into a bone are improved, and such that the instrument it easier to use for a surgeon.

This object is achieved according to the invention by means of a handling instrument of the type mentioned at the outset, which is characterized in that the outer housing part comprises at least one guide slot that extends in the axial longitudinal direction and that passes through a wall of the housing part, in that the inner rod part, in the region of the guide slot of the outer housing part, comprises a transverse opening that extends in particular in the radial direction, and in that a coupling element can be arranged in said transverse opening of the inner rod part arranged in the outer housing part, the coupling element projecting into the guide slot of the outer housing part or projecting outwards through the guide slot and in both cases being slidable in the longitudinal direction in the guide slot such that the inner rod part and the outer housing part are arranged so as to be shiftable in the axial longitudinal direction relative to one another, but in a rotationally fixed manner on account of the coupling element, and such that the rod part can be loaded in the axial longitudinal direction by means of the coupling element.

The outer housing part and the inner rod part of the handling instrument according to the invention are therefore coupled together in a rotationally fixed manner by means of the coupling element. The torque for screwing in the bone screw is thus transmitted both via the rod part that engages in a tool placement point of the bone screw and via the outer housing part. By means of the coupling element, it is possible to shift the rod part relative to the housing part in the axial longitudinal direction and to thus load said rod part in the longitudinal direction. By distally shifting the rod part relative to the housing part in the longitudinal direction, it is possible to brace the rod part and housing part with respect to the bone screw. Preferably, means are provided for connecting the outer housing part to the bone screw.

It is conceivable for the coupling element to be pivotally held on the rod part, and as a result to be able to pivot radially from the inside into the guide slot of the housing part.

According to an advantageous embodiment of the invention, the transverse opening of the rod part is an insertion opening into which the coupling element can be inserted from the outside in the radial direction through the guide slot of the outer housing part. The rod part is arranged in the housing part such that the insertion opening of the rod part is positioned behind the guide slot of the housing part. As a result, the coupling element can be inserted from the outside in the radial direction into the insertion opening of the inner rod part arranged in the housing part.

According to another advantageous embodiment of the invention, the guide slot of the outer housing part has a slot width that varies in the longitudinal direction. As a result, insertion of the coupling element is facilitated and the guide function for the coupling element is ensured.

In this regard, it proves advantageous if the coupling element tapers radially outwards when inserted and can be inserted or removed through the guide slot of the outer housing part into the insertion opening of the inner rod part in at least one particular position, preferably the position having the greatest slot width. The tapered radially outer end region of the coupling element is preferably slidable in the guide slot over the entire extent thereof in the axial longitudinal direction. On account of the radially outward tapering and the varying width of the guide slot, the coupling element is arranged in the housing part in a captive manner.

According to another concept of the invention, a locking sleeve comprising an insertion opening for the coupling element can be arranged concentrically between the outer housing part and the inner rod part, and the transverse opening in the rod part is an elongate opening that extends in the axial direction, such that the locking sleeve can be shifted in the axial longitudinal direction relative to the rod part and/or housing part by means of the coupling element. The coupling element can preferably be inserted radially from the outside through the guide slot of the outer housing part and through the insertion opening of the locking sleeve into the elongate opening of the rod part. The coupling element can be slid in the elongate opening of the inner rod part and in the guide slot of the outer housing part in the axial longitudinal direction. As a result, the locking sleeve can be shifted relative to the rod part and/or housing part in the axial longitudinal direction until the transversely extending coupling part strikes the end of the elongate hole of the rod part in each case.

In another advantageous embodiment of the invention, the inner rod part, in particular by means of a spring, can be distally prestressed in the longitudinal direction relative to the outer housing part. The spring is in particular arranged in a proximal end region in the housing part and acts on the rod part distally in the longitudinal direction. By means of the coupling element, the rod part can be loaded against the force of the spring or in the direction of the force of the spring.

According to another particularly important concept of the invention, the outer housing part comprises an external threaded portion that is interrupted by the guide slot, onto which external threaded portion a threaded sleeve comprising an internal threaded portion can be screwed.

In this regard, it proves advantageous if the coupling element can be moved distally and proximally in the longitudinal direction relative to the outer housing part by means of the threaded sleeve being screwed on and off, respectively. It is conceivable for the coupling element arranged in a slidable manner in the guide slot of the housing part to be pushed by a distal or proximal end face of the threaded sleeve in the longitudinal direction distally or proximally, respectively.

According to another advantageous embodiment of the handling instrument according to the invention, the threaded sleeve comprises an insertion opening for the coupling element. The coupling element can therefore be inserted radially from the outside through the insertion opening of the threaded sleeve screwed onto the outer housing part and through the guide slot of the housing part and optionally through the insertion opening of the locking sleeve into the transverse opening of the rod part.

In a development of the invention, it proves advantageous if the radially outer end of the coupling element that projects out through the guide slot of the outer housing part engages in an internal circumferential groove in the threaded sleeve, such that the threaded sleeve is arranged so as to be rotatable in the circumferential direction with respect to the outer housing part even when the coupling element is inserted. If the coupling element engages in the internal circumferential groove, the threaded sleeve can carry out a relative movement in the circumferential direction with respect to the coupling element and the rod and housing part, arranged so as to be mutually rotationally fixed on account of the coupling element, or the locking sleeve. By engaging in the circumferential groove, the coupling element is shifted in the axial longitudinal direction relative to the outer housing part and/or the inner rod part when the threaded sleeve is screwed on or off. In this way, the rod part and/or the locking sleeve can be shifted in the axial longitudinal direction by means of the threaded sleeve.

According to another particularly important concept of the invention, a toggle lever mechanism is provided on the outer housing part, the toggle lever mechanism comprising a first and a second lever element and the first lever element being connected in an articulated manner to the second lever element via a toggle joint and the first lever element being pivotally supported on the outer housing part and the second lever element being supported on the coupling element, and the toggle lever mechanism being movable from a bent state into a stretched state and vice versa by actuating an operating element, such that by actuating the toggle lever mechanism, the coupling element can be moved in the longitudinal direction distally or proximally relative to the outer housing part. It proves advantageous if the first and/or second lever element is designed in the shape of a half-shell and surrounds the outer housing part in the manner of a half-shell in the stretched state of the toggle lever mechanism and preferably adjoins said housing part.

The first lever element that is pivotally supported on the outer housing part can be pivoted by means of the operating element. The movement is transmitted to the coupling element arranged in a slidable manner in the guide slot of the housing part via the second lever element that is connected in an articulated manner to the first lever element. In this way, a pivoting movement of the operating element is converted into a distal or proximal linear movement of the coupling element in the longitudinal direction, and it is possible to shift the rod part relative to the housing part in the axial longitudinal direction and to load said rod part. In the stretched state, the tensioning force of the toggle lever mechanism is transmitted to the rod part via the coupling element and the rod part and housing part can be braced with respect to the bone screw.

It proves advantageous that the second lever element comprises at least one receiving opening for the coupling element. Advantageously, the radially outer end of the coupling element that projects out through the guide slot of the outer housing part engages in the receiving opening of the lever element.

In a development of the invention, it proves advantageous that the toggle lever mechanism comprises a resilient element that is preferably formed on the first or second lever element or is formed of the first or second lever element. Advantageously, prestress is transmitted to the rod part by means of the resilient element via the coupling element when the toggle lever mechanism is closed, i.e. when the toggle lever mechanism is moved into the stretched state. In the stretched state of the toggle lever mechanism, the resilient element is compressed by between 0.1 mm and 5 mm, preferably between 0.5 mm and 2 mm. Preferably, a force of 100 N (Newton) to 10 kN, preferably 250 N to 5 kN, can be generated by means of the toggle lever mechanism. When the toggle lever mechanism is released, i.e. when the toggle lever mechanism is moved into the bent state, the prestress is initially maintained and only decreases when the toggle lever mechanism is opened to a sufficient extent.

Advantageously, the first or second lever element has braces that, in a side view, are arranged in the shape of a trapezium, triangle or arc, in particular in the shape of a C-arc, and that are rigidly interconnected at one end and at the other end are not interconnected or in any case not rigidly interconnected. Preferably, by pressing the free, or in any case not rigidly interconnected, ends of the braces together, a prestressing force builds up.

According to another advantageous embodiment of the invention, in a distal end region, the outer housing part comprises two approximately half-shell-shaped portions that are arranged so as to be diametrically opposite one another in the longitudinal direction, that are delimited by a gap formed therebetween that extends in the longitudinal direction and that can be deflected away from one another slightly transversely to the longitudinal direction, such that they can enter a rear engagement position on the head of the bone screw, in particular such that they can latch or snap in, and in the process receive between one another at least part of the head of the bone screw. The half-shell-shaped portions advantageously engage behind at least part of the bone screw in the axial longitudinal direction and in the circumferential direction.

According to another advantageous embodiment of the invention, the inner rod part or the locking sleeve arranged concentrically between the rod part and the housing part comprises at least one transverse pin, which projects radially from the inside into the gap between the two approximately half-shell-shaped portions, such that by proximally moving the inner rod part or the locking sleeve in the longitudinal direction relative to the outer housing part, the transverse pin runs against slopes delimiting the gap and thus spreads the half-shell-shaped portions apart.

In this way, it is possible to adjust the transverse pin, which projects into the gap between the two half-shell-shaped portions, by means of the coupling element in the longitudinal direction and, by proximally shifting the coupling element in the axial longitudinal direction, to move the half-shell-shaped portions apart. In this spread-apart state of the half-shell-shaped portions, the head of the bone screw can be inserted between the two portions. When shifting the coupling element distally, the transverse pin is moved away by the slopes, and the half-shell-shaped portions return, or spring back, to their starting position and engage behind part of the head of the bone screw.

It proves advantageous that, by means of the rod part engaging in the tool placement point on the bone screw and by means of the rear engagement in the circumferential direction or in the axial longitudinal direction of the outer housing part on the head of the bone screw, the housing part and the rod part can be braced with respect to one another and with respect to the bone screw. If the two half-shell-shaped portions are in a rear engagement position with the head of the bone screw, and the rod part that engages in the tool placement point on the bone screw is further shifted distally in the longitudinal direction, the rod part and the housing part are braced with respect to one another as a result. In this way, the threaded shaft of the bone screw is also braced with respect to the head of the bone screw, and the torque for screwing in the bone screw can be transmitted both via the head of the bone screw and via the tool placement point.

According to another advantageous embodiment of the invention, a locking element is provided which engages over the half-shell-shaped portions of the outer housing part at least in part such that the half-shell-shaped portions are prevented from spreading apart at least in part. Preferably, the locking element engages over the half-shell-shaped portions when said portions are in a rear engagement position with the bone screw and release of the rear engagement is intended to be prevented.

According to a preferred embodiment, the in particular annular locking element is held on the transverse pin of the rod part or locking sleeve. In this way, the locking element can be shifted in the axial direction by shifting the rod part or the locking sleeve by means of the coupling element. Distal shifting of the coupling element in the axial direction and an accompanying shift of the transverse pin and locking element cause the half-shell-shaped portions to move out of a widened position back into the initial state thereof and the locking element locks the portions against inadvertently spreading apart.

According to another advantageous embodiment of the handling instrument according to the invention, at least one radial cut-out is formed in the outer housing part, through which cut-out a marking on an outer face of the inner rod part or on an outer face of the locking sleeve can be visually perceived if the inner rod part or the locking sleeve is in a particular position relative to the outer housing part in the longitudinal direction. This allows the desired correct positioning of the inner rod part or locking sleeve in the longitudinal direction relative to the outer housing part.

According to another advantageous embodiment of the invention, the inner rod part and preferably the coupling element are cannulated in the axial longitudinal direction, such that a guide wire can be guided through therein. For example, a guide wire of this kind can be guided through the handling instrument and the bone screw, which guide wire is secured in advance in a particular position on the bone such that the bone screw can be positioned and screwed in at the right place on the bone.

According to another advantageous embodiment of the handling instrument according to the invention, the outer housing part comprises, on the proximal end, one or more tool placement points, such that a suitable tool can be attached such that the handling instrument can be rotated about the longitudinal direction in order to screw the threaded shaft of the bone screw into or out of a bone.

Other advantages, features and details of the invention will become apparent from the dependent claims and from the diagrammatic illustrations and following description of the preferred embodiments shown in the figures.

In the drawings:

FIG. 7 shows the handling instrument according to the invention in a fourth preferred embodiment.

The figures show a handling instrument according to the invention generally denoted by the reference sign 10. In accordance with a first embodiment according to FIG. 1, the handling instrument 10 comprises a housing part 14 that extends in the longitudinal direction 12 and a rod part 16 that extends in the longitudinal direction 12, and a coupling element 18 that extends transversely between said housing part and said rod part, and a threaded sleeve 20.

Figure 1:
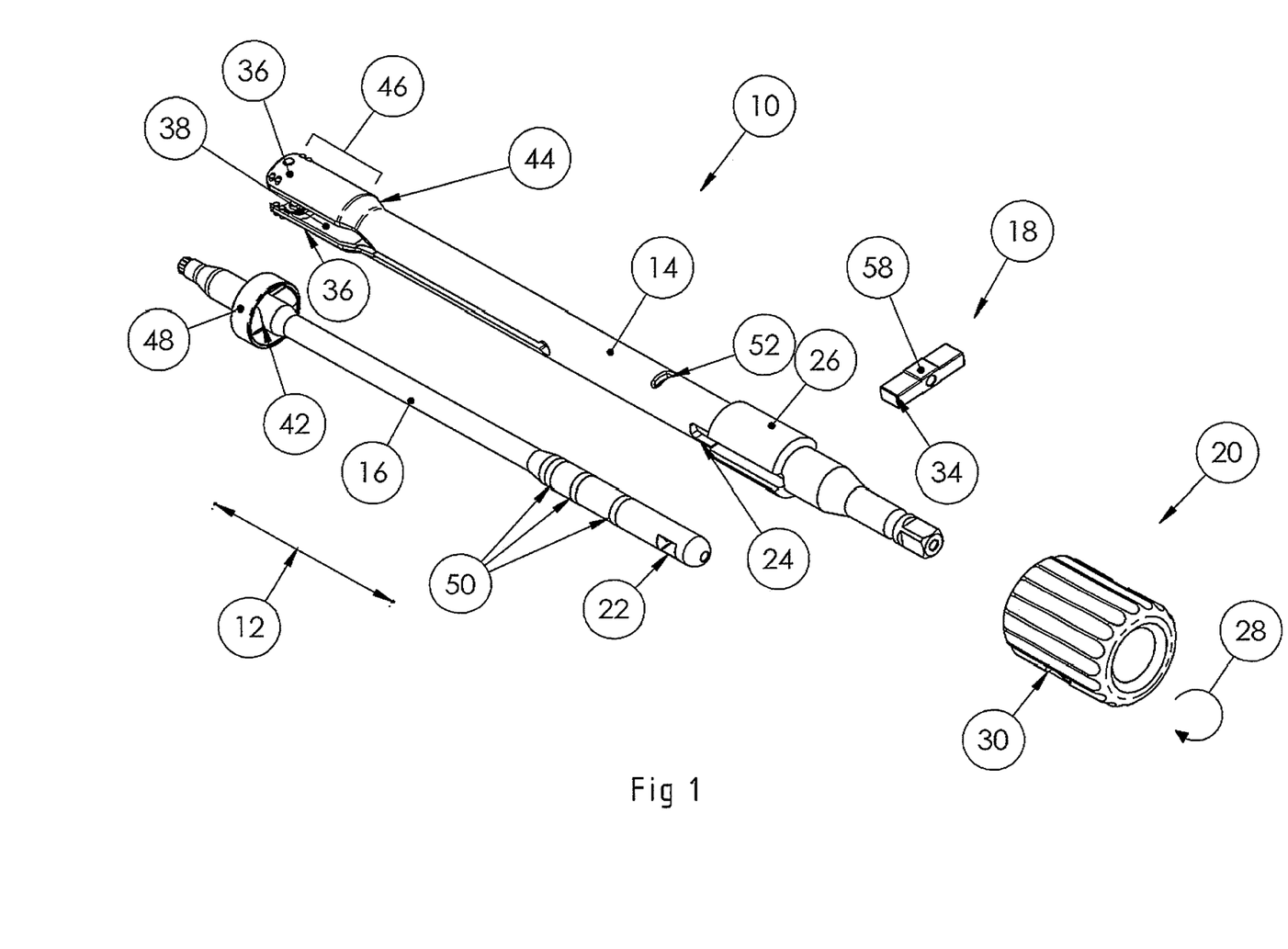
FIG. 1 shows the handling instrument according to the invention in a first preferred embodiment.

The housing part 14 is approximately tubular or sleeve-shaped at least in portions and is designed such that the rod part 16 can be inserted into the outer housing part 14 in the longitudinal direction 12.

In order to be able to arrange the rod part 16 in the housing part 14 in a rotationally fixed manner, the rod part 16 comprises a transverse opening 22 and the housing part 14 comprises a guide slot 24. In the example embodiment shown, the coupling element 18 can be inserted radially from the outside through the guide slot 24 of the housing part 14 into the transverse opening 22 of the rod part 16 arranged in the housing part 14. When inserted, the coupling element 18 projects into the guide slot 24 and is arranged therein so as to be slidable in the longitudinal direction. In this way, the rod part 16 is rotationally fixed in the housing part 14 on account of the coupling element 18 but can be shifted relative to the housing part 14 in the longitudinal direction 12. By shifting the coupling element 18 in the longitudinal direction 12, the rod part 16 can be shifted relative to the housing part 14. It is conceivable for the rod part 16 to be able to be prestressed relative to the housing part 14, in particular by means of a spring (not shown here).

The housing part 14 comprises an external thread 26. The external thread 26 extends in a circumferential direction 28 and is interrupted in the region of the guide slot 24 of the housing part 14. The threaded sleeve 20 can be screwed onto the external thread 26. The threaded sleeve 20 comprises an insertion opening 30 for the coupling element 18 and an internal circumferential groove 32 (see FIG. 3b). The coupling element 18 can be inserted radially from the outside through the insertion opening 30 of the threaded sleeve 20 screwed onto the outer housing part 14 and through the guide slot 24 of the housing part 14 into the transverse opening 22 of the rod part 16. When inserted, a radially outer end 34 of the coupling element 18 projects on both sides radially outwards through the guide slot 24 of the housing part 14 and engages in the internal circumferential groove 32 of the threaded sleeve 20. When screwing the threaded sleeve 20 on or off, said threaded sleeve carries out a relative movement in the circumferential direction 28 with respect to the coupling element 18 and the rod and housing part 14, which are arranged in a rotationally fixed manner with respect to one another on account of the coupling element 18. The coupling element 18 is shifted in the longitudinal direction 12 relative to the outer housing part 14 when the threaded sleeve 20 is screwed on or off. In this way, the rod part 16 can be shifted in the longitudinal direction 12 relative to the housing part 14 by means of the threaded sleeve 20.

Figure 2A:
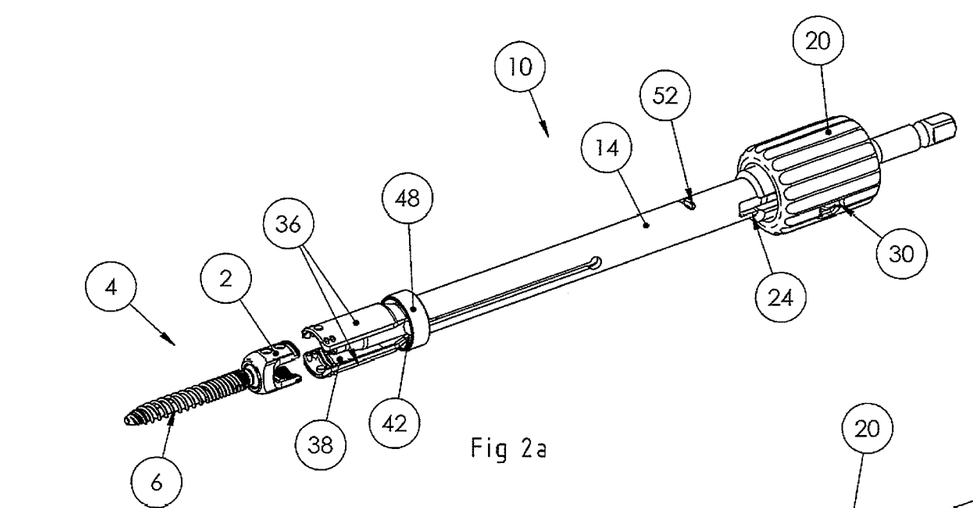
FIGS. 2a and 2b show the handling instrument according to FIG. 1 in various handling steps.
Figure 2B:
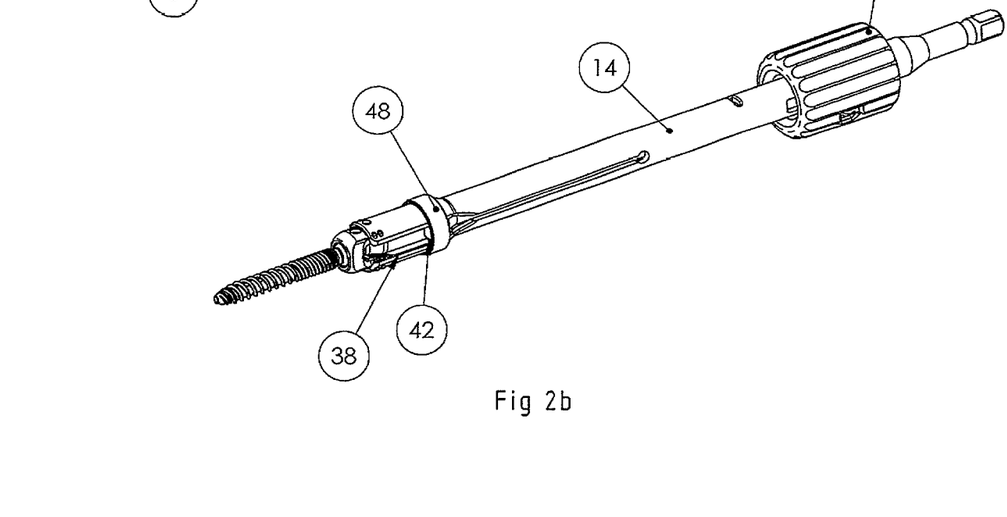

The housing part 14 comprises two approximately half-shell-shaped portions 36 that are arranged so as to be diametrically opposite one another and that are delimited by a gap 38 formed therebetween that extends in the longitudinal direction 12. The half-shell-shaped portions 36 can be deflected away from one another slightly transversely to the longitudinal direction 12. In this way, the two portions 36 can enter a rear engagement position on the head 2 of the bone screw 4 and in the process receive between one another at least part of the head 2 of the bone screw 4 (see FIG. 2b).

The rod part 16 comprises two transverse pins 42 which extend radially from the inside from the rod part 16 arranged in the outer housing part 14 radially outwards into the gap 38 that delimits the half-shell-shaped portions 36. If the rod part 16 is shifted proximally in the longitudinal direction 12 relative to the housing part 14, the transverse pins 42 run against the slopes 44 delimiting the gap 38. The two half-shell-shaped portions 36 are spread apart from one another transversely to the longitudinal direction 12 as a result (see FIG. 2a). In this spread-apart state, the half-shell-shaped portions 36 can receive between one another at least part of the head 2 of the bone screw 4 and enter a rear engagement position with part of the bone screw head 2 by springing or snapping back. It is conceivable for means to be provided in a distal end region 46 of the half-shell-shaped portions 36 that can cooperate with complementary means on the bone screw head 2, in particular engage therein, latch therein or snap therein, and for the half-shell-shaped portions 36 to enter a rear engagement position with the bone screw head 2 in the longitudinal direction 12 and preferably also in the circumferential direction 28 by means of the means cooperating in this manner.

In order for the half-shell-shaped portions 36 to be able to enter a rear engagement position with the head 2 of the bone screw 4, the rod part 16 is shifted distally in the longitudinal direction 12 relative to the housing part 14 by means of the coupling element 18. As a result, the transverse pins 42 move away from the slopes 44 and the two half-shell-shaped portions 36 spring back towards one another again. The rod part 16 is moved further distally in the longitudinal direction 12 until it engages in a tool placement point on the threaded shaft 6 of the bone screw 4. On account of the rear engagement position of the housing part 14 with the head 2 of the bone screw 4 and on account of the engagement of the rod part 16 in the tool placement point on the threaded shaft 6, the housing part 14 and the rod part 16 can be prestressed relative to one another and relative to the bone screw 4. Furthermore, the rod part 16 and the housing part 14 are arranged in a rotationally fixed manner with respect to one another on account of the coupling element 18 inserted into the guide slot 24 and transverse opening 22 and on account of the transverse pins 42 engaging in the gap 38. In this way, the torque for screwing in the bone screw 4 can be introduced both via the housing part 14 and via the rod part 16.

An annular locking element 48 is arranged on the transverse pins 42 of the rod part 16. If the rod part 16 is shifted distally in the longitudinal direction 12, the locking element 48 is pushed over the distal end region 46 of the sleeve-shaped portions 36. The locking element 48 engages over the portions 36 such that said portions are locked against spreading apart and the rear engagement position cannot be inadvertently released.

Furthermore, the rod part 16 comprises a plurality of markings 50 on an outer face thereof and the housing part 14 comprises a cut-out 52 through which the markings 50 are visible. As a result, it is possible to determine the relative shifting between the rod part 16 and the housing part 14 in the longitudinal direction 12.

Figure 3A:
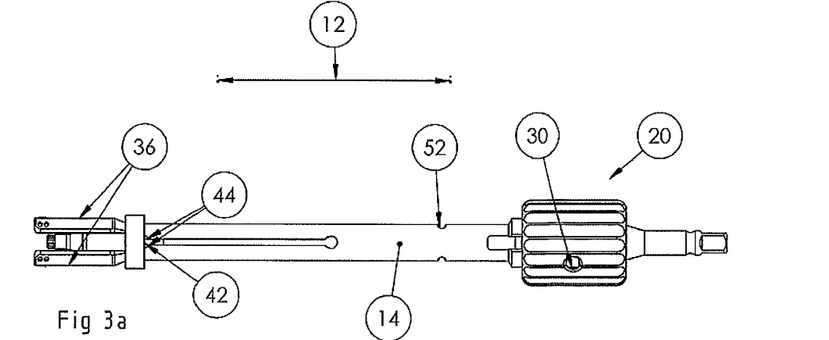
FIG. 3a shows the handling instrument according to FIG. 1 in a side view.
Figure 3B:
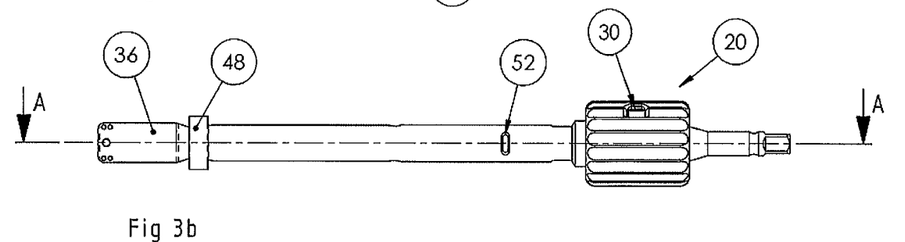
FIG. 3b shows the handling instrument according to FIG. 1 in a plan view.
Figure 3C:
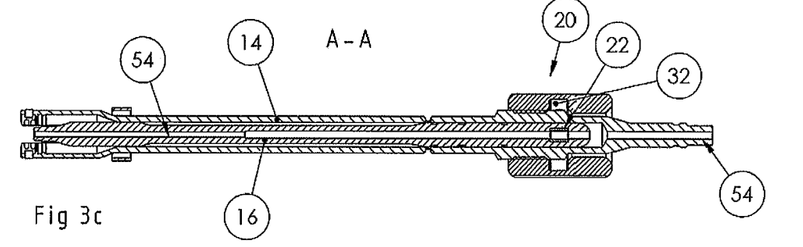
FIG. 3c shows the handling instrument according to FIG. 1 in a sectional view along A-A from FIG. 3b.

FIG. 3c shows a sectional view of the handling instrument 10 according to the invention according to a section along A-A (see FIG. 3b). The rod part 16, the housing part 14 and the coupling element 18 (see FIG. 3e) comprise a through-opening 54 that extends in the longitudinal direction 12 and as a result are cannulated in the longitudinal direction 12. A guide wire, for example, can be guided through in the through-opening 54 through the handling instrument 10 and the bone screw 4, which guide wire is secured in advance in a particular position on the bone, such that the bone screw 4 can be positioned and screwed into the bone at the right place.

Figure 3D:
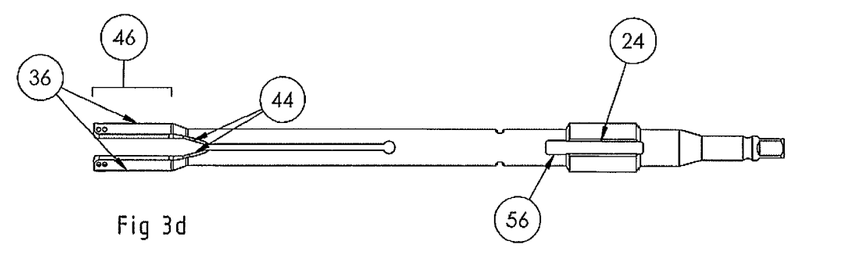
FIG. 3d shows part of the handling instrument according to FIG. 1.
Figure 3E:
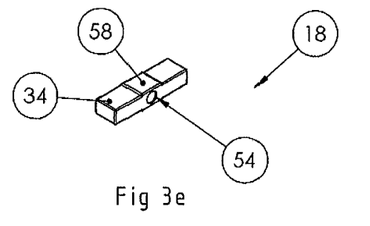
FIG. 3e shows another part of the handling instrument according to FIG. 1.

FIG. 3d is a side view of the housing part 14. The guide slot 24 has a width that varies in the longitudinal direction 12. The slot width varies in particular between 1.5 mm and 20 mm, in particular between 2 mm and 10 mm. In the example embodiment shown, the width of the guide slot 24 decreases proximally in the longitudinal direction 12 starting from a distal end 56 having the greatest width. The coupling element 18 tapers radially outwards and the cross section of the coupling element 18 increases radially inwards starting from the radially outer end 34. On account of the increase in cross section 58, the coupling element 18 can only be inserted through the guide slot 24 in one position: in the embodiment shown on the distal end 56 of said guide slot. The tapered radially outer end 34 of the coupling element 18 can be slid across the entire length of the guide slot 24 in the longitudinal direction 12. The coupling element 18 is arranged in the housing part 14 such that it cannot fall out on account of the increase in cross section 58.

Figure 4:
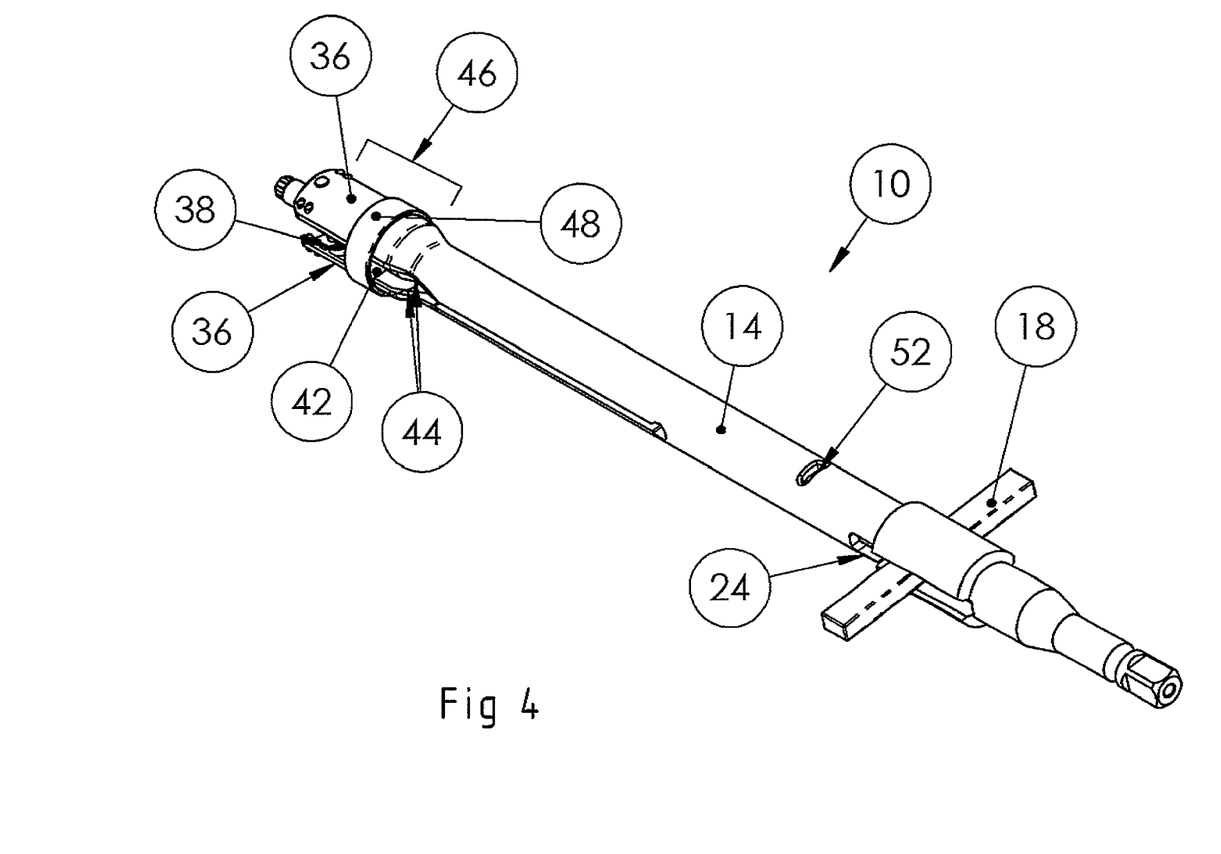
FIG. 4 shows the handling instrument according to the invention in a second preferred embodiment.

FIG. 4 shows the handling instrument 10 according to a second preferred embodiment. The rod part 16 is arranged so as to be rotationally fixed, on account of the coupling element 18, but so as to slide in the housing part 14 relative thereto in the longitudinal direction 12. Preferably, the rod part 16 is distally prestressed relative to the housing part 14 by means of a spring. If the coupling element is, for example, manually retracted proximally in the longitudinal direction 12, the locking of the half-shell-shaped portions 36 is released and the half-shell-shaped portions 36 are moved apart by means of the transverse pins 42, which run against slopes 44 delimiting the gap 38. The head 2 of the bone screw 4 or at least part of it can now be arranged between the two half-shell-shaped portions 36. If the coupling element 18 is no longer being pulled proximally counter to the prestressing force, the prestressing force acting distally in the longitudinal direction 12 pushes the rod part 16 distally relative to the housing part 14 in the longitudinal direction 12. The rod part 16 finally engages in a tool placement point of the bone screw 4 and the housing part 14 engages behind part of the head 2 of the bone screw 4 by means of the half-shell-shaped portions 36. On account of the prestressing force acting on the rod part 16 and the rear engagement position of the housing part 14 with the bone screw 4, the rod part 16 and the housing part 14 are braced with respect to one another and with respect to the bone screw 4.

Figure 5:
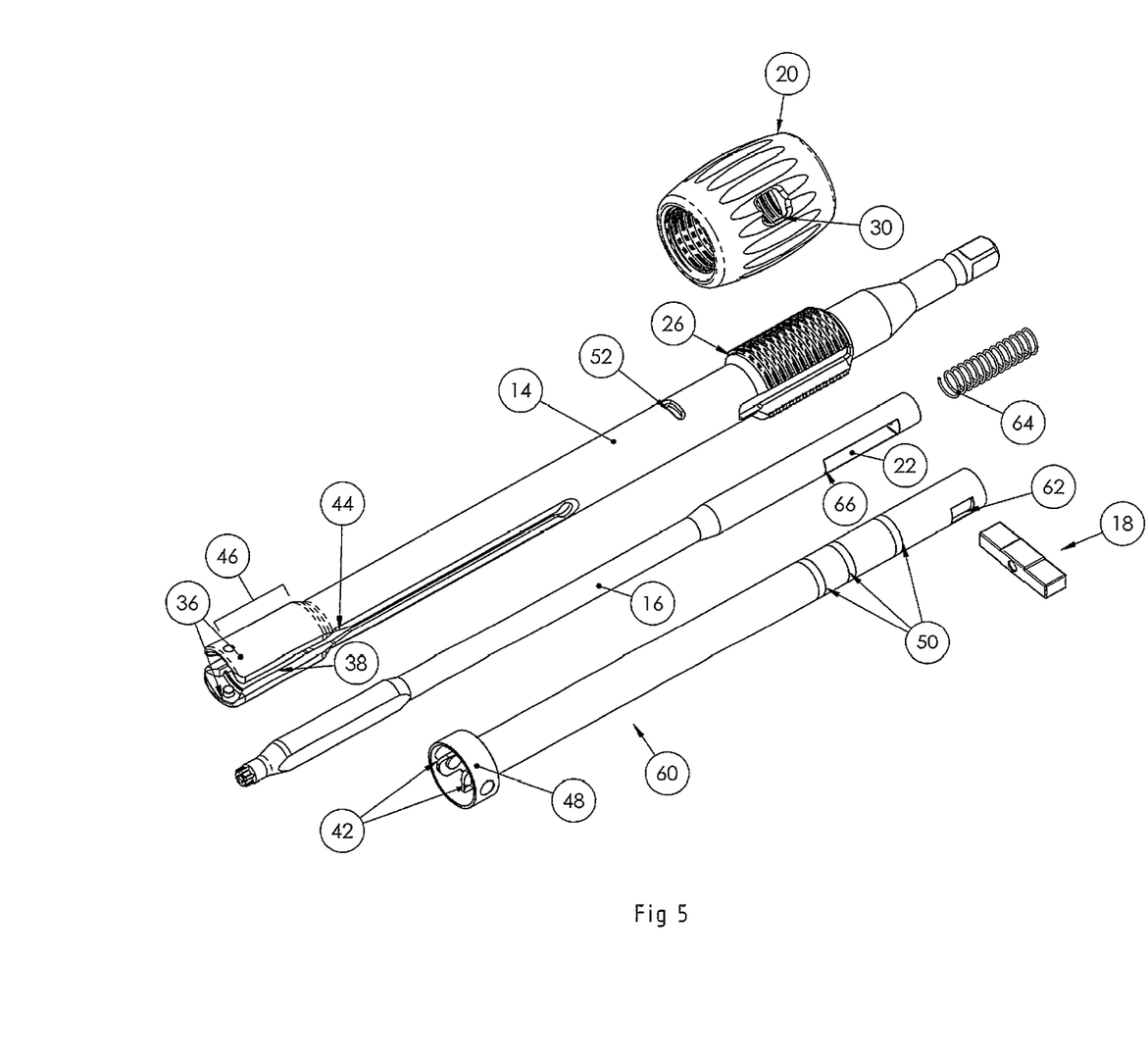
FIG. 5 shows the handling instrument according to the invention in a third preferred embodiment.

FIG. 5 shows the handling instrument 10 according to a third preferred embodiment. The handling instrument 10 comprises an additional locking sleeve 60 that extends in the longitudinal direction 12 and that can be inserted into the housing part 14 in the longitudinal direction 12. The locking sleeve 60 can therefore be arranged concentrically between the rod part 16 and the housing part 14. The locking sleeve 60 also comprises an insertion opening 62 for the coupling element 18. In this way, the locking sleeve 60 can be arranged so as to be rotationally fixed in the housing part 14, on account of the coupling element 18, but so as to be shiftable relative to the housing part 14 in the longitudinal direction 12. By shifting the coupling element 18 in the longitudinal direction 12, the locking sleeve 60 can be shifted relative to the housing part 14. The transverse pins 42 for spreading apart the half-shell-shaped portions 36 and the locking element 48 for securing the rear engagement position of the housing part 14 with the head 2 of the bone screw 4 are arranged on the locking sleeve 60 in this embodiment. In this case, too, the half-shell-shaped portions 36 are spread apart and locked by means of shifting of the coupling element 18 and an accompanying shift of the locking sleeve 36 when the threaded sleeve 20 is screwed on and off.

The transverse opening 22 of the rod part 16 for inserting the coupling element 18 is, in this case, however, designed as an elongate opening having an extension in the longitudinal direction 12. In this way, the locking sleeve 60 can be shifted relative to the rod part 16 in the longitudinal direction 12. The rod part 16 can be prestressed distally relative to the housing part 14 by means of a spring 64.

Figures 6A, 6B, 6C, 6D:
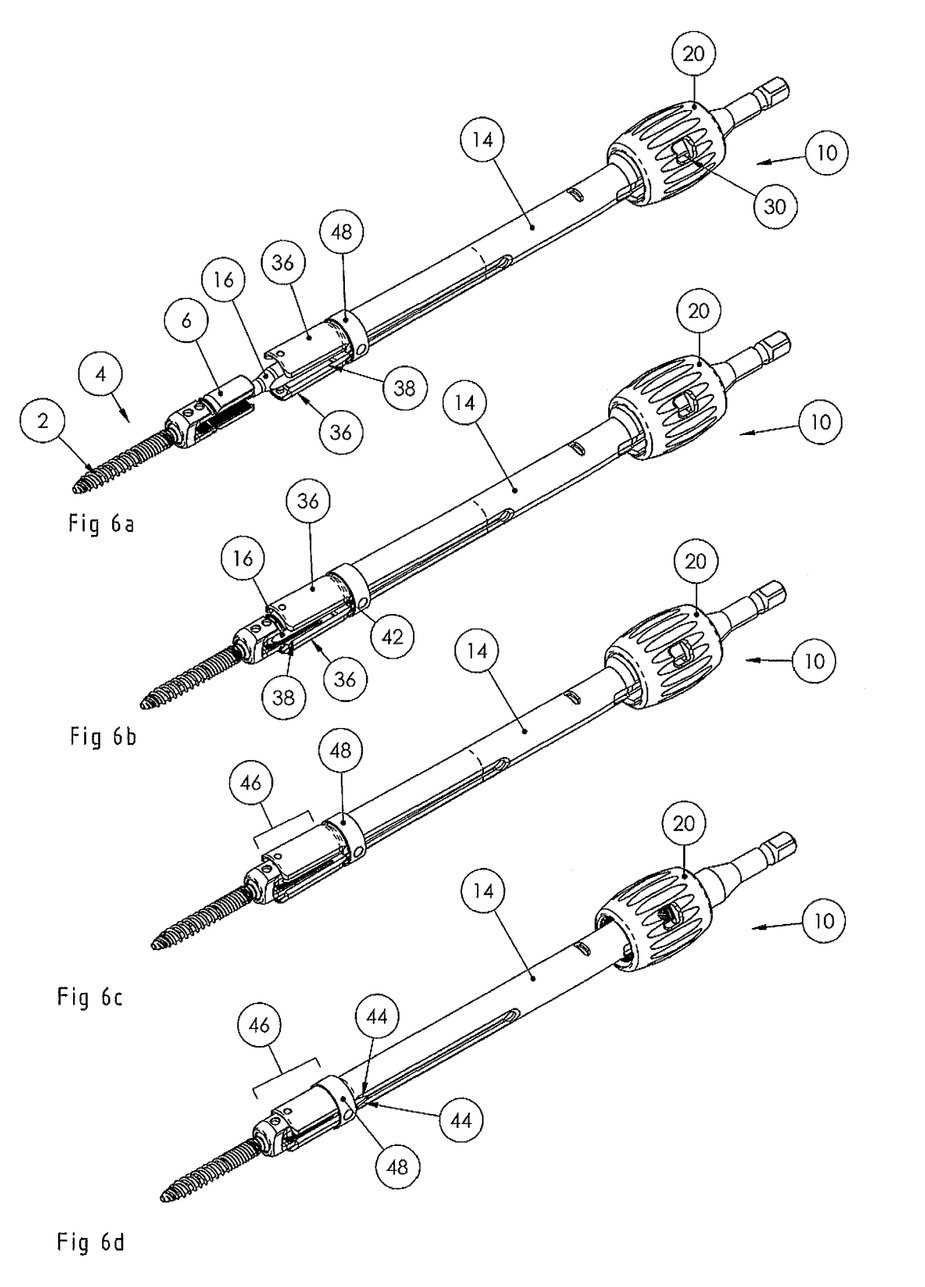
FIGS. 6a to 6d show the handling instrument according to FIG. 5 in various handling steps.

FIGS. 6a to 6d show the handling instrument 10 in various handling steps. In FIG. 6a, the locking sleeve 60 is shifted proximally in the longitudinal direction 12 relative to the housing part 14 and rod part 16 by means of the threaded sleeve 20. The transverse pins 42 arranged on the locking sleeve 60 run against slopes 44 which delimit the gap 38. As a result, half-shell-shaped portions 36 are moved apart transversely to the longitudinal direction 12. The rod part 16 is prestressed by means of the spring 64 and is pushed distally relative to the housing part 14 by means of the prestressing force. The rod part 16 engages in the tool placement point on the threaded shaft 6 of the bone screw 4 (FIG. 6b). In order for the head 2 of the bone screw 4 to be able to be arranged between the half-shell-shaped portions 36 and to enter a rear engagement position therewith, the rod part 16 is loaded proximally counter to the prestressing force in the longitudinal direction 12 by means of the bone screw 4 (FIG. 6c). Subsequently, the coupling element 18 and thus also the locking sleeve 60 are moved distally by means of the threaded sleeve 20. The half-shell-shaped portions 36 spring back and thus enter a rear engagement position with the bone screw 4. The annular locking element 48 then engages over the half-shell-shaped portions 36. The coupling element 18 is shifted distally further until it comes into abutment with a distal end 66 of the elongate opening 22 and therefore loads the rod part 16 beyond the distally acting spring force. In this way, the rod part 16 can be braced with respect to the housing part 14 in rear engagement with the head 2 of the bone screw 4 and with respect to the bone screw 4. The torque for screwing in the bone screw 4 can be introduced via the head 2 and the tool placement point of the bone screw 4.

Figure 8A:
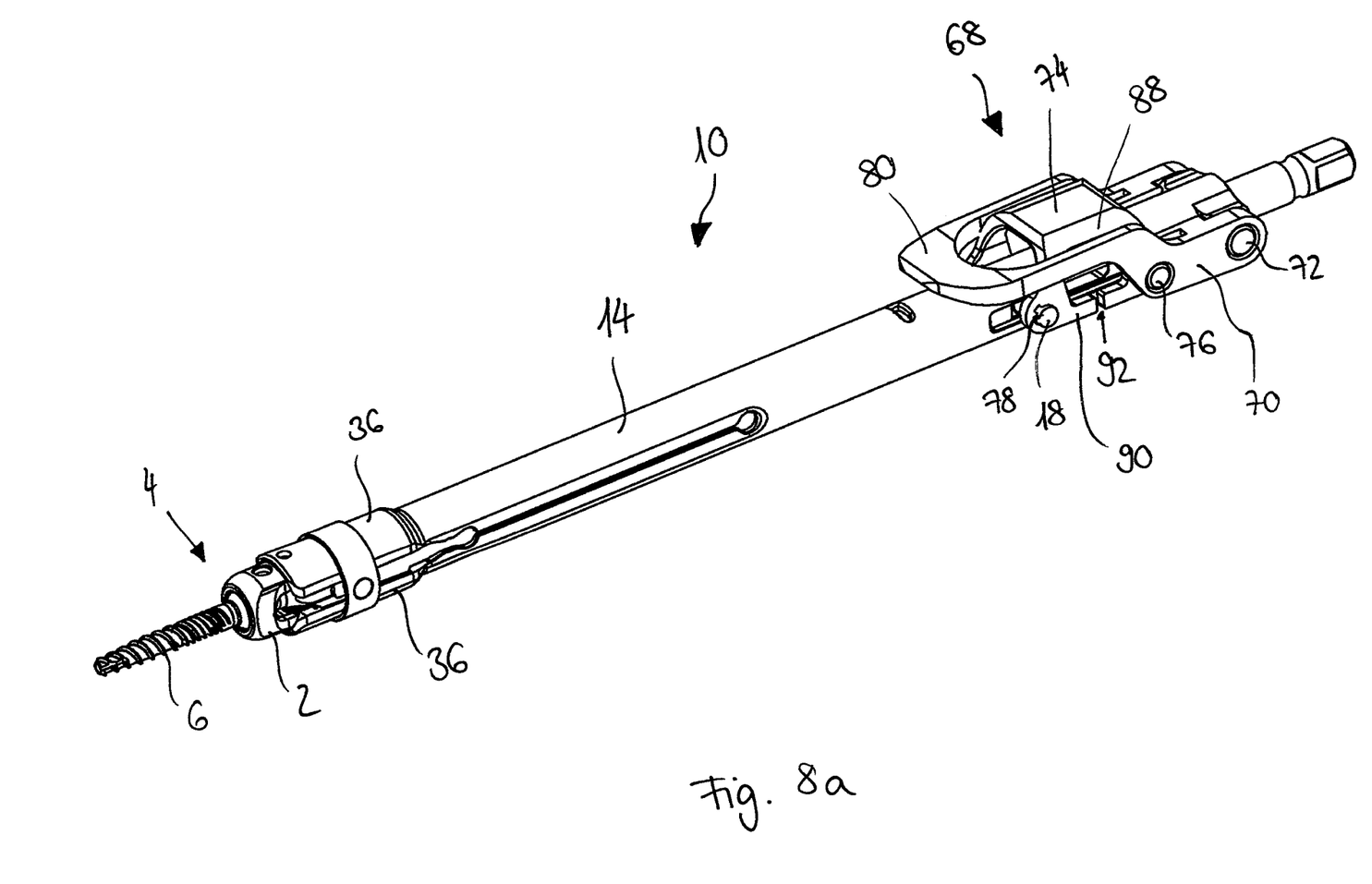
FIGS. 8a and 8b show the handling instrument according to FIG. 7 in various handling steps.
Figure 8B:
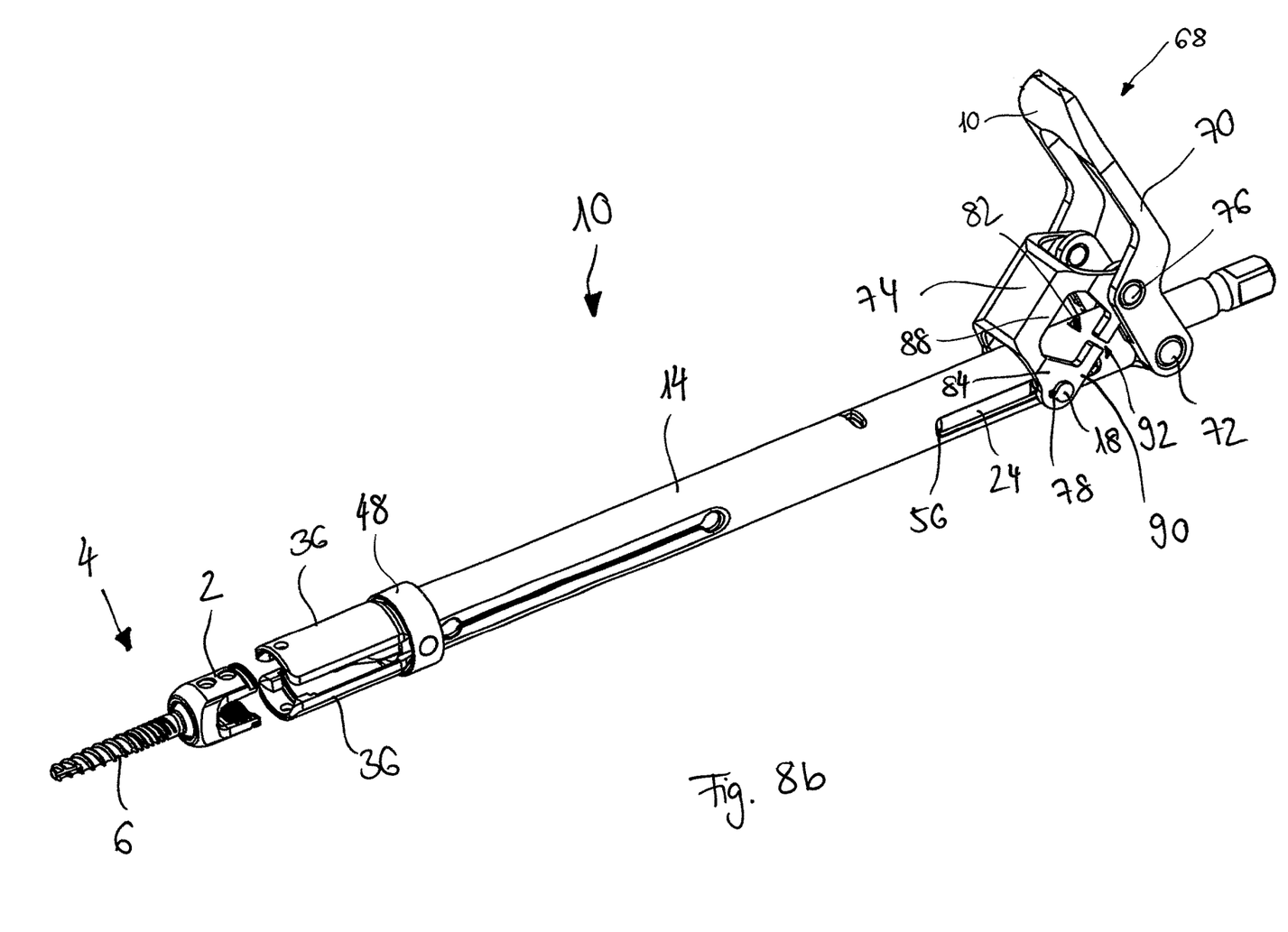

FIG. 7 shows the handling instrument 10 according to a fourth embodiment. The rod part 16 is arranged so as to be rotationally fixed, on account of the coupling element 18, but so as to be slidable in the housing part 14 relative thereto in the longitudinal direction 12. In order to shift the coupling element 18, the handling instrument 10 comprises a toggle lever mechanism 68. The toggle lever mechanism comprises a first lever element 70, which is supported on the housing part 14 so as to be pivotable about a pivot pin 72. A second lever element 74 is connected in an articulated manner to the first lever element 70 by means of a toggle joint 76 (FIGS. 8a and 8b). The second lever element 74 comprises two receiving openings 78 for the coupling element 18. If the coupling element 18 is arranged in the guide slot 24 of the housing part 14, the radially outer ends of the coupling element 18 that project through the guide slot 24 of the outer housing part 14 engage in the receiving openings 78 of the second lever element 74.

The toggle lever mechanism 68 can be moved out of a bent state (FIG. 8a) into a stretched state (FIG. 8b) and vice versa by actuating an operating element 80. The first lever element pivotally supported on the outer housing part 14 is pivoted about the pivot pin 72 by means of the operating element 80. Said pivoting movement is transmitted via the toggle joint 76 to the second lever element 74 and thus to the coupling element 18, the coupling element 18 carrying out a distal or proximal linear movement in the longitudinal direction.

In the embodiment shown, the coupling element 18 is inserted radially from the outside through the guide slot 24 of the housing part 14 into the transverse opening 22 of the rod part 16 arranged in the housing part 14. If the coupling element 18 is then moved by means of the toggle lever mechanism 68 in the guide slot 24, the rod part 16 is shifted relative to the housing part 14 in the axial longitudinal direction 12 and is loaded.

In the stretched state of the toggle lever mechanism 68, the tensioning force of the toggle lever mechanism 68 is transmitted via the coupling element 18 to the rod part 16 and the rod part 16 and the housing part 14 can be braced with respect to the bone screw 4.

The toggle lever mechanism 68 further comprises a resilient element 82. According to the embodiment shown, the resilient element 82 is formed on the second lever element 74. The second lever element 74 comprises two braces 84, 86 on each side that, in a side view, are arranged in the shape of a trapezium and that, at one end, i.e. on an upper base side 88, are rigidly interconnected and at the other end, i.e. on a lower base side 90, are not interconnected, such that a gap 92 is formed on the lower base side 90.

The first brace 84 comprises the receiving opening 78 for the coupling element 18, such that the second lever element 74 is supported on the coupling element via the first brace 84. Via the second brace 86, the second lever element 74 is connected to the first lever element 70 via the toggle joint 76. When closing the toggle lever mechanism, the brace 86 is pushed towards the brace 84 and thus a prestressing force builds up. Said prestressing force is transmitted via the coupling element 18 to the rod part 16. In the stretched state of the toggle lever mechanism 86, the resilient element 82 is compressed in particular by between 0.1 mm and 5 mm, preferably between 0.5 mm and 2 mm. Preferably, a force of 100 N (newton) to 10 kN, preferably 250 N to 5 kN, can be generated by means of the toggle lever mechanism 68. When the toggle lever mechanism 68 is released, i.e. when the toggle lever mechanism 68 moves out of the stretched into the bent state, the prestress is initially maintained and only decreases when the toggle lever mechanism 68 is opened to a sufficient extent. The gap 92 prevents the resilient element 82 from being overloaded in that the gap 92 also functions as a stop.

In a distal region of the handling instrument 10, the rod portion 16 comprises two transverse pins 42 which extend radially from the inside from the rod portion 16 arranged in the outer housing part 14 radially outwards into a gap 38 delimiting the half-shell-shaped portions 36. If the rod portion 16 is shifted proximally relative to the housing part 14 in the longitudinal direction 12, the transverse pins 42 run against slopes 44 delimiting the gap 38. As a result, the two half-shell-shaped portions 36 are spread apart transversely to the longitudinal direction 12 (see FIG. 8b). In this spread-apart state, the half-shell-shaped portions 36 can receive between one another at least part of the head 2 of the bone screw 4, and by springing or snapping back enter a rear engagement position with part of the bone screw head 2.

If the coupling element 18 is retracted proximally in the longitudinal direction 12 by means of opening the toggle lever mechanism 68, the locking of the half-shell-shaped portions 36 is released and the half-shell-shaped portions 36 are spread apart by means of the transverse pins 42, which run against slopes 44 delimiting the gap 38. The head 2 of the bone screw 4 or at least part thereof can then be arranged between the two half-shell-shaped portions 36. If the coupling element 18 is moved distally by closing the toggle lever mechanism, the tensioning force of the toggle lever mechanism acting distally in the longitudinal direction 12 pushes the rod part 16 relative to the housing part 14 distally in the longitudinal direction 12. The rod part 16 finally engages in a tool placement point of the bone screw 4 and the housing part 14 engages behind part of the head 2 of the bone screw 4 by means of the half-shell-shaped portions 36. On account of the tensioning force acting on the rod part 16 and on account of the rear engagement position of the housing part 14 with the bone screw 4, the rod part 16 and the housing part 14 are braced with respect to one another and with respect to the bone screw 4.

FIGS. 8a and 8b show the handling instrument 10 from FIG. 7 in various handling steps. In FIG. 8a, the toggle lever mechanism 68 is in a bent state, i.e. in an open state. By actuating the operating element 80, the pivoting movement of the first lever element 70 is transmitted to the second lever element 74 and thus to the coupling element 18. When the toggle lever mechanism 68 closes, i.e. when the toggle lever mechanism 68 is brought out of the bent state and into a stretched state, the coupling element 18 moves distally. When the toggle lever mechanism opens i.e. when the toggle lever mechanism 68 is brought out of bent state and into a stretched state, the coupling element 18 moves proximally.

What is claimed is:

1. Handling instrument for a bone screw, comprising a threaded shaft and a head, and it being possible to connect the handling instrument to the bone screw in a releasable yet rigid and rotationally fixed manner, such that the threaded shaft of the bone screw can be screwed into a bone by means of the handling instrument, said handling instrument comprising an outer housing part that extends in an axial longitudinal direction, is designed at least in portions in the shape of a tube and comprises a wall, and said handling instrument comprising an inner rod part that is arranged in the outer housing part, the inner rod part being able to engage in a torque-absorbing tool placement point of the bone screw, characterized in that the outer housing part comprises at least one guide slot that extends in the axial longitudinal direction and that passes through a wall of the housing part, in that the inner rod part, in the region of the guide slot of the outer housing part, comprises a transverse opening that extends in the radial direction, and in that a coupling element can be arranged in said transverse opening of the inner rod part arranged in the outer housing part, the coupling element projecting into at least one of the guide slot of the outer housing part or outwards through the guide slot and in both cases being slidable in the longitudinal direction in the guide slot such that the inner rod part and the outer housing part are arranged so as to be shiftable in the axial longitudinal direction relative to one another, but in a rotationally fixed manner on account of the coupling element and such that the rod part can be loaded in the axial longitudinal direction by means of the coupling element, said handling instrument further comprising a locking sleeve comprising an insertion opening for the coupling element can be arranged concentrically between the outer housing part and the inner rod part, and in that the transverse opening in the rod part is an elongate opening that extends in the longitudinal direction, such that the locking sleeve can be shifted in the axial longitudinal direction relative to the rod part and/or housing part by means of the coupling element.

2. Handling instrument according to claim 1, characterized in that the transverse opening of the rod part is an insertion opening into which into which the coupling element can be inserted from the outside in the radial direction through the guide slot of the outer housing part.

3. Handling instrument according to claim 1, characterized in that the guide slot has a slot width that varies in the longitudinal direction.

4. Handling instrument according to claim 3, characterized in that the coupling element tapers radially outwards, and the coupling element can be inserted or removed through the guide slot of the outer housing part into the insertion opening of the inner rod part in at least one particular position.

5. Handling instrument according to claim 1, characterized in the inner rod part, in particular by means of a spring, can be distally prestressed in the axial longitudinal direction relative to the outer housing part.

6. Handling instrument according to claim 1, characterized in that the outer housing part comprises an external threaded portion which is interrupted by the guide slot and onto which a threaded sleeve comprising an internal threaded portion can be screwed.

7. Handling instrument according to claim 6, characterized in that the coupling element can be moved distally and proximally in the longitudinal direction relative to the outer housing part by means of the threaded sleeve being screwed on and off, respectively.

8. Handling instrument according to claim 6, characterized in that the threaded sleeve comprises an insertion opening for the coupling element.

9. Handling instrument according to claim 6, characterized in that the radially outer end of the coupling element that projects out through the guide slot of the outer housing part engages in an internal circumferential groove in the threaded sleeve, such that the threaded sleeve is arranged so as to be rotatable with respect to the outer housing part.

10. Handling instrument according to claim 1, characterized in that a toggle lever mechanism is provided on the outer housing part, the toggle lever mechanism comprising a first and a second lever element and the first lever element being connected in an articulated manner to the second lever element via a toggle joint and the first lever element being pivotally supported on the outer housing part and the second lever element being supported on the coupling element, and the toggle joint mechanism being movable from a bent state into a stretched state and vice versa by actuating an operating element, such that by actuating the toggle lever mechanism, the coupling element can be moved in the longitudinal direction distally and proximally relative to the outer housing part.

11. Handling instrument according to claim 10, characterized in that the second lever element comprises at least one receiving opening for the coupling element.

12. Handling instrument according to claim 10, characterized in that the toggle lever mechanism comprises a resilient element which is preferably formed on the first or second lever element or is formed of the first or second lever element.

13. Handling instrument according to claim 12, characterized in that at least one of the first or second lever element comprises braces that, in a side view, are arranged in the shape of one of a trapezium, triangle or arc, and that are rigidly interconnected at one end and at the other end are not interconnected or in any case not rigidly interconnected.

14. Handling instrument according to claim 1, characterized in that the outer housing part, in a distal end region, comprises two approximately half-shell-shaped portions that are arranged in the longitudinal direction so as to be diametrically opposite one another, that are delimited by a gap formed there between extending in the longitudinal direction, and that can be deflected away from one another slightly transversely to the longitudinal direction, such that they can enter a rear engagement position on the head of the bone screw, in particular such that they can latch or snap in, and in the process receive between one another at least part of the head of the bone screw.

15. Handling instrument according to claim 1, characterized in that the inner rod part or the locking sleeve arranged concentrically between the rod part and the housing part comprises at least one transverse pin, which projects radially from the inside into the gap between the two approximately half-shell-shaped portions, such that by proximally moving the inner rod part or the locking sleeve in the longitudinal direction relative to the outer housing part, the at least one transverse pin runs against slopes delimiting the gap and thus spreads the half-shell-shaped portions apart.

16. Handling instrument according to claim 1, characterized in that, by means of the rod part engaging in the tool placement point on the bone screw and by means of the rear engagement in the circumferential direction or in the axial longitudinal direction of the outer housing part on the head of the bone screw, the housing part and the rod part can be braced with respect to one another and with respect to the bone screw.

17. Handling instrument according to claim 1, wherein the outer portion comprises half shell shaped portions, and characterized in that a locking element is provided which engages over the half-shell-shaped portions of the outer housing part at least in part such that the half-shell-shaped portions are prevented from spreading apart at least in part.

18. Handling instrument according to claim 17, further comprising an annular locking element and at least one transverse pin of the rod part or locking sleeve, characterized in that the annular locking element is held on the at least one transverse pin of the rod part or locking sleeve.

19. Handling instrument according to claim 1, characterized in that at least one radial cut-out is formed in the outer housing part, through which cut-out at least one of a marking on an outer face of the inner rod part or on an outer face of the locking sleeve can be visually perceived if the inner rod part is in a particular position relative to the outer housing part in the longitudinal direction.

20. Handling instrument according to claim 1, characterized in that the inner rod part are cannulated in the axial longitudinal direction, such that a guide wire can be received therein.

21. Handling instrument according to claim 1, characterized in that the outer housing part comprises one or more tool placement points at the proximal end and a suitable tool can be attached such that the handling instrument can be rotated about the axial longitudinal direction in order to screw the threaded shaft of the bone screw into or out of a bone.

22. Handling instrument for a bone screw, comprising a threaded shaft and a head, and it being possible to connect the handling instrument to the bone screw in a releasable yet rigid and rotationally fixed manner, such that the threaded shaft of the bone screw can be screwed into a bone by means of the handling instrument, said handling instrument comprising an outer housing part that extends in an axial longitudinal direction, is designed at least in portions in the shape of a tube and comprises a wall, and said handling instrument comprising an inne rod part that is arranged in the outer housing part, the inner rod part being able to engage in a torque-absorbing tool placement point of the bone screw, characterized in that the outer housing part comprises at least one guide slot that extends in the axial longitudinal direction and that passes through a wall of the housing part, in that the inner rod part, in the region of the guide slot of the outer housing part, comprises a transverse opening that extends in the radial direction, and in that a coupling element can be arranged in said transverse opening of the inner rod part arranged in the outer housing part, the coupling element projecting into at least one of the guide slot of the outer housing part or outwards through the guide slot and in both cases being slidable in the longitudinal direction in the guide slot such that the inner rod part and the outer housing part are arranged so as to be shiftable in the axial longitudinal direction relative to one another, but in a rotationally fixed manner on account of the coupling element and such that the rod part can be loaded in the axial longitudinal direction by means of the coupling element, said handling instrument further comprising a toggle lever mechanism is provided on the outer housing part, the toggle lever mechanism comprising a first and a second lever element and the first lever element being connected in an articulated manner to the second lever element via a toggle joint and the first lever element being pivotally supported on the outer housing part and the second lever element being supported on the coupling element, and the toggle joint mechanism being movable from a bent state into a stretched state and vice versa by actuating an operating element, such that by actuating the toggle lever mechanism, the coupling element can be moved in the longitudinal direction distally and proximally relative to the outer housing part.

23. Handling instrument according to claim 22, characterized in that the second lever element comprises at least one receiving opening for the coupling element.

24. Handling instrument according to claim 22, characterized in that the toggle lever mechanism comprises a resilient element which is preferably formed on the first or second lever element or is formed of the first or second lever element.

25. Handling instrument according to claim 24, characterized in that at least one of the first or second lever element comprises braces that, in a side view, are arranged in the shape of one of a trapezium, triangle or arc, and that are rigidly interconnected at one end and at the other end are not interconnected or in any case not rigidly interconnected.

* * * * *